United States Patent
Kelly et al.

(10) Patent No.: US 6,312,736 B1
(45) Date of Patent: Nov. 6, 2001

(54) HERBAL COMPOSITION TO RELIEVE PAIN

(75) Inventors: Gregory J. Kelly, Glastonbury, CT (US); Ann Perry, Bayshore, NY (US)

(73) Assignee: Biotech Corporation, Glastonbury, CT (US)

( * ) Notice: Subject to any disclaimer, the term of this patent is extended or adjusted under 35 U.S.C. 154(b) by 0 days.

(21) Appl. No.: 09/456,694

(22) Filed: Dec. 9, 1999

(51) Int. Cl.[7] .................. A61K 35/78; A61K 91/127
(52) U.S. Cl. .................. 424/734; 424/764; 424/769; 424/775; 424/450
(58) Field of Search .................. 424/195.1, 400, 424/434, 435, 450, 734, 764, 769, 775

(56) References Cited

U.S. PATENT DOCUMENTS

| | | |
|---|---|---|
| 4,377,567 | 3/1983 | Geho ......................................... 424/1 |
| 4,921,644 | 5/1990 | Lau ........................................ 264/4.1 |
| 5,171,571 | 12/1992 | Stephan et al. . |
| 5,296,224 | 3/1994 | Schwabe . |
| 5,401,502 | 3/1995 | Wunderlich et al. . |
| 5,512,285 | 4/1996 | Wilde . |
| 5,869,540 | 2/1999 | Smith .................................. 514/783 |
| 5,891,465 | * 4/1999 | Keller et al. ......................... 424/450 |

FOREIGN PATENT DOCUMENTS

| | | |
|---|---|---|
| 96/22774 | * 8/1996 | (WO) . |
| 98/39018 | * 9/1998 | (WO) . |

OTHER PUBLICATIONS

Peirce, A. Am. Pharm. Assoc.—Practical Guide to Herbal Medicines, pp. 320–322 & 373–375, 1998.*
Castleman, M. The Healing Herbs, Rodale Press, PA, pp. 186–189 & 369–371, 1991.*
Product Alert—Alvista Herbal RemeTeas, Migra–Wonder Abstract, Jul. 1996.*

* cited by examiner

*Primary Examiner*—Christopher R. Tate
(74) *Attorney, Agent, or Firm*—Cummings & Lockwood

(57) ABSTRACT

An herbal composition is used to relieve pain and other symptoms associated with migraines and other types of headaches. The preferred herbal composition includes white willow bark extract, kava kava root extract, feverfew extract, ginger root extract, Guarana extract, and Vitamin B6. The herbal composition may be combined with liposomes to carry the composition. The result is an herbal composition that can be applied sublingually for rapid, effective pain relief.

8 Claims, No Drawings

HERBAL COMPOSITION TO RELIEVE PAIN

FIELD OF THE INVENTION

The present invention relates generally to herbal compositions, and more particularly, to herbal compositions for relieving pain associated with headaches, and combinations of such herbal compositions and liposomes to permit delivery of such compositions through a spray applied under the tongue.

BACKGROUND OF THE INVENTION

STEPHAN, et al., U.S. Pat. No. 5,171,571, relates to methods for producing effervescent tablets containing extract from willow bark. The effervescent tablet acts as a carrier of the active ingredients from the willow bark extract and permits more rapid resorption of the active substances in the body. STEPHAN's method does not teach or suggest combining willow bark extract with other herbal ingredients. In addition, STEPHAN's method is limited to administration of the active ingredients by dissolving an effervescent tablet in water. Nor does Stephen's method teach or suggest the use of liposomes for delivery of willow bark extract in a spray.

SCHWABE, U.S. Pat. No. 5,296,224, shows a method for producing a dry extract from kava kava of at least 50% by weight. The extract produced by SCHWABE's method is claimed to have good solubility in water and high bioavailability after oral administration. SCHWABE's method is directed only to production of dry extract from kava kava, and does not teach or suggest the use of kava kava extract alone or in combination with other substances, in a formulation to relieve pain. In addition, SCHWABE does not teach or suggest the use of liposomes for delivery of kava kava extract in a spray.

SMITH, U.S. Pat. No. 5,869,540, shows an herbal treatment for improving the appearance of skin comprising oral administration and topical application for valerian root extract. SMITH also discusses uses for feverfew extract, ginger root extract and willow bark extract. SMITH does not disclose, however, the use of combinations of these herbal components for pain relief. In addition, SMITH does not teach or suggest use of liposomes for delivery of herbal treatments in a spray.

GEHO, U.S. Pat. No. 4,377,567, shows the use of lipid membrane structures to carry drugs to the liver for treatment of diabetes or viral hepatitis. GEHO does not teach or suggest the use of liposomes to carry an herbal composition for treatment of headaches.

LAU, et al., U.S. Pat. No. 4,921,644, shows a liposome with a strong positive charge that will bind to mucin tissue. LAU is generally directed toward the structure of the liposome, and expressly disclaims the use of liposomes in combination with any particular composition. LAU does not each or suggest the use of liposomes as a carrier for an herbal composition for treatment of headaches.

It is an object of the present invention to overcome one or more of the above-described drawbacks or disadvantages of the prior art. It is a further object of the present invention to combine white willow bark extract, kava kava extract, and at least one of feverfew and ginger root extract in a composition that provides relief from pain and other symptoms associated with headaches. The composition can be further combined with liposomes to permit delivery of the composition through a spray applied under the tongue.

SUMMARY OF THE INVENTION

The present invention provides, in one aspect, a remedy for pain caused by headaches or migraine headaches. The invention comprises a combination of white willow bark extract, kava kava extract, and at least one of feverfew and ginger root extract. This combination provides the advantage of rapidly relieving pain and reducing symptoms caused by headaches. The herbal composition can be further combined with liposomes, which act as a carrier for the herbal composition and permit delivery through a spray applied under the tongue.

The present invention combines the extracts of white willow bark, kava kava root and at least one of feverfew and ginger root. The extract of white willow bark contains salicinum, which reduces pain caused by headaches. The extract of kava kava root acts as a mild sedative, and induces physical and mental relaxation. Feverfew and/or ginger root extract are included to reduce nausea and upset stomachs that frequently are associated with headaches. In the preferred embodiment of the invention, the composition is comprised of the herbal ingredients in the following approximate proportions relative to each other: about 55% by weight willow bark extract, about 33% by weight feverfew and ginger root extracts, and about 12% by weight kava kava root extract. However, it should be understood that the invention is not limited in this regard, and the relative amounts of these ingredients can be varied to achieve similar results.

Among the advantages of the invention is that the composition is comprised of ingredients that have a strong direct or indirect effect on the relief of pain and other symptoms caused by headaches. A further advantage of the invention is that it is comprised of all natural ingredients, which are fast-acting in providing relief of pain and other symptoms.

In accordance with the second aspect of the present invention, the combination of herbal ingredients can be further combined with liposomes, which act as a carrier of the herbal composition. Preferably, the resulting combination is delivered through a spray applied under the tongue. Among the advantages of using liposomes to deliver the composition are the resulting rapid absorption of the active ingredients, and the ease of use. In addition, the liposomal spray of the invention can be carried by a person and used when needed to provide pain relief in seconds.

Other objects and advantages of the present invention will become apparent in view of the following detailed description of preferred embodiments.

DETAILED DESCRIPTION OF THE PREFERRED EMBODIMENTS

The present invention is directed to a novel herbal composition that provides relief from headache pain. The effect of the herbal composition on pain relief can be made relatively rapid by delivering the herbal composition through a liposomal spray applied under the tongue.

The herbal composition of the invention preferably comprises white willow bark extract, kava kava root extract, and at least one of feverfew and ginger root extract. White willow bark contains salicin, which has pain-relieving effects like aspirin, but typically with fewer side effects. Salicin reduces pain by inhibiting prostaglandin synthesis in sensory nerves. Kava kava is an herb that induces physical and mental relaxation. The active ingredients act as muscle relaxants and anti-convulsants. Kava kava root extract is a mood elevator and a mild sedative that reduces anxiety, stress, restlessness and facilitates sleep.

Feverfew (Tanacetum Parthenium) has been shown to reduce the frequency and severity of migraines, as well as frequently associated symptoms of nausea and vomiting.

Feverfew is used in the composition of the invention to help prevent migraine headaches. Guarana is a natural form of caffeine that acts as a mild stimulant. It helps relieve headaches and migraine headaches and reduce hunger.

Thus, each of these herbal ingredients produces effects that are beneficial in reducing pain and/or other physical symptoms, and moreover, the combination of these substances in the proportions discussed below results in a composition that is uniquely beneficial for reducing the pain and discomfort caused by headaches, particularly migraine headaches.

In the preferred embodiment of the invention, the extract from white willow bark is combined with kava kava extract and at least one of ginger root and feverfew. The white willow bark extract provides salicin, a natural pain reliever. Kava kava root extract is a natural mild sedative that reduces anxiety, stress, restlessness and facilitates sleep. Feverfew extract or ginger root extract are included to reduce nausea and upset stomach frequently associated with migraine headaches.

The active ingredients can be combined in any number of ways to optimize the desired effects. In the preferred embodiment of the invention, however, the ingredients are combined such that one recommended dose of the composition provides the following approximate quantity of each ingredient:

| | |
|---|---|
| White Willow Bark Extract | 225 mg |
| Feverfew Extract | 135 mg |
| Ginger Root Extract | 10 mg |
| Kava Kava Root Extract | 50 mg |
| Guarana Extract | 125 mg |
| Vitamin B6 (as pyridoxine hydrochloride) | 1 mg |

However, as may be recognized by those skilled in the pertinent art based on the teachings herein, the exact formulation can be varied to provide increases or decreases in particular effects. The present inventors have learned that the relative proportions of the active ingredients can be varied up or down by as much as approximately 20%, and the resulting composition will continue to provide relief from headache pain and discomfort. Therefore, the ingredients in the herbal composition may be present in the following approximate ranges such that one recommended dose of the composition provides quantities of the ingredients within the following approximate ranges:

| | |
|---|---|
| White Willow Bark Extract | 180–270 mg |
| Feverfew/Gingeroot Extract | 110–150 mg |
| Kava Kava Root Extract | 40–60 mg |

As shown in the preferred embodiment above, other ingredients may be added to the ingredients included in the preferred embodiment to provide additional relief or other benefits. For example, Guarana extract may be added to provide additional relief from migraines and other types of headaches. Vitamin B6 may be included to assist in metabolism of amino acids and fatty acids.

The herbal composition may be combined with liposomes in a manner known to those of ordinary skill in the pertinent art based on the teachings herein so that the liposomes act as carriers of the herbal composition. The liposomes containing the herbal composition can then be administered in any number of ways known to those of ordinary skill in the pertinent art based on the teachings herein. One such method of delivery is by means of a spray applied under the tongue. Further methods of delivery of liposomal compositions are described in LAU, U.S. Pat. No. 4,921,644, and in GEHO, U.S. Pat. No. 4,377,567, both of which are hereby expressly incorporated by reference as part of the present disclosure. The liposomal spray allows the active ingredients to be absorbed quickly into the body, thereby providing rapid relief from the pain and other symptoms associated migraines and other types of headaches.

As will be recognized by those of ordinary skill in the pertinent art based on the teachings herein, numerous changes and modifications may be made to the above-described and other embodiments of the invention without departing from its scope as defined in the appended claims. For example, the relative quantities of the ingredients may be varied to achieve different desired effects, additional ingredients may be added, and/or similar ingredients may be substituted for one or more of the ingredients described. Accordingly, this detailed description of preferred embodiments is to be taken in an illustrative as opposed to a limiting sense.

What is claimed is:

1. An herbal composition for relief of headache pain and other symptoms associated with headaches comprising:

from about 46% to about 64% by weight of white willow bark extract;

from about 8% to about 18% by weight of Kava Kava root extract; and from about 25% to about 41% by weight of at least one of feverfew extract and ginger root extract.

2. An herbal composition as defined in claim 1, further comprising Guarana extract.

3. An herbal composition as defined in claim 1, further comprising Vitamin B6.

4. An herbal composition as defined in claim 2, further comprising Vitamin B6.

5. An herbal composition as defined in claim 1, combined with liposomes for administration of the herbal composition.

6. An herbal composition combined with liposomes as defined in claim 5, wherein the herbal composition further comprises Guarana extract.

7. An herbal composition combined with liposomes as defined in claim 5, wherein the herbal composition further comprises Vitamin B6.

8. An herbal composition combined with liposomes as defined in claim 6, wherein the herbal composition further comprises Vitamin B6.

\* \* \* \* \*